United States Patent
Jaunakais

Patent Number: 5,620,658
Date of Patent: Apr. 15, 1997

[54] COLORIMETRIC TEST STRIP

[75] Inventor: Ivars Jaunakais, Rock Hill, S.C.

[73] Assignee: Industrial Test Systems, Inc., Rock Hill, S.C.

[21] Appl. No.: 526,849

[22] Filed: Sep. 11, 1995

[51] Int. Cl.⁶ .................................................. G01N 31/22
[52] U.S. Cl. ................... 422/58; 422/61; 436/109
[58] Field of Search .................... 422/56–58, 61; 436/169

[56] References Cited

U.S. PATENT DOCUMENTS

| | | |
|---|---|---|
| 3,006,735 | 10/1961 | Jordan . |
| 3,748,096 | 7/1973 | Schmitt et al. . |
| 3,901,657 | 8/1975 | Lightfoot . |
| 4,092,115 | 5/1978 | Rupe et al. . |
| 4,275,031 | 6/1981 | Fischer et al. . |
| 4,904,605 | 2/1990 | O'Brien et al. . |
| 5,491,094 | 2/1996 | Ramana et al. .......................... 436/125 |
| 5,516,488 | 5/1996 | Bunce et al. .............................. 422/56 |

OTHER PUBLICATIONS

Quantofix® Iron 100 Instructions Sheet, date unknown.

*Primary Examiner*—Lyle A. Alexander
*Attorney, Agent, or Firm*—Timothy R. Kroboth

[57] ABSTRACT

A novel immersible colorimetric test strip is provided. The test strip includes a flow through, colorimetric indicator-bearing carrier, and a substance separately carried on the test strip for chemically modifying analyte into a detectible ionic form for color development of the indicator. Also provided are a test kit and an analysis method for using the kit.

19 Claims, 1 Drawing Sheet

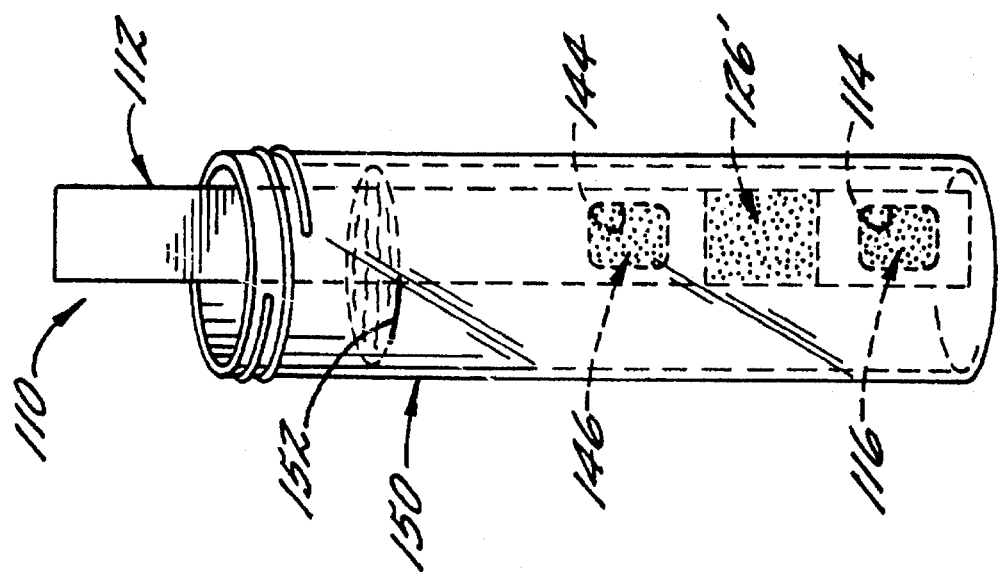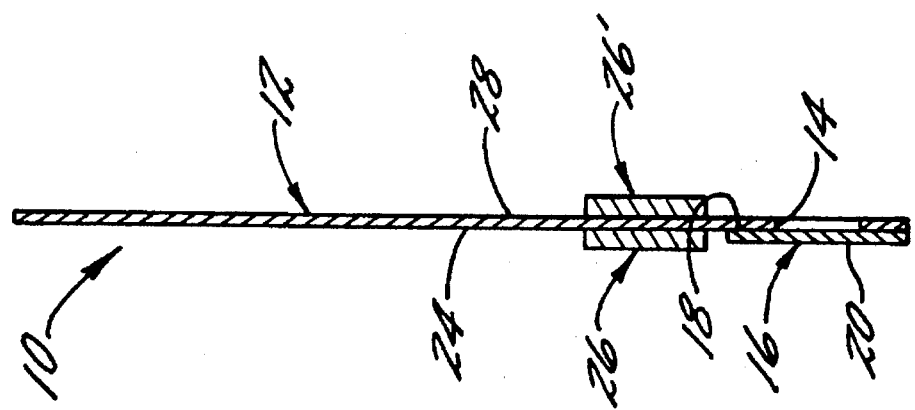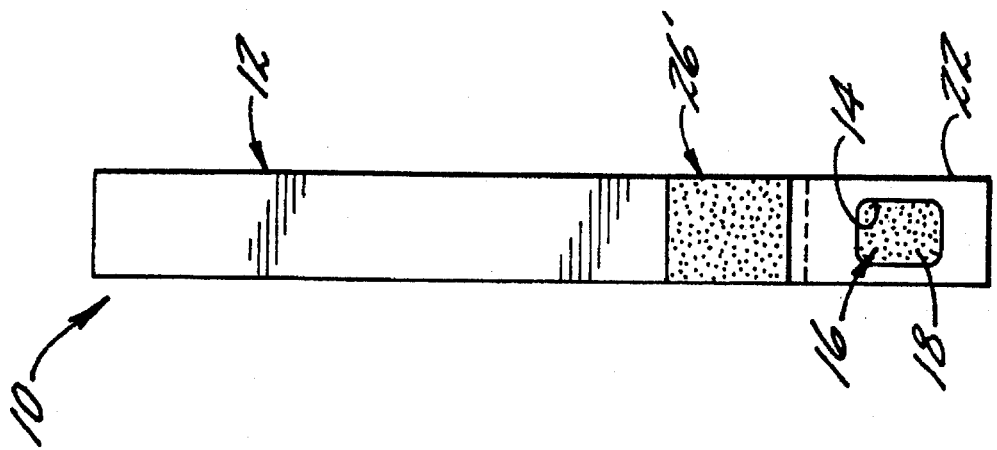

COLORIMETRIC TEST STRIP

FIELD OF THE INVENTION

This invention relates to an immersible colorimetric test strip.

BACKGROUND OF THE INVENTION

Colorimetric test strips or reagent strips for water analysis are known. Areas of use include tap water quality testing, industrial and environmental testing, pool and spa testing, lake and stream testing, aquarium testing and other types of water testing. Simple, quick and accurate testing is advantageous, and a test strip must have the necessary detection capability.

For analysis of copper or iron cations, these test strips typically consist of a plastic support having affixed thereto a porous, absorbent carrier bearing an appropriate indicator. Illustrative is the copper (I)-detecting test stick of U.S. Pat. No. 3,748,096, in which the absorbent carrier is impregnated with an indicator composition that includes a reducing agent for converting copper (II) to copper (I). Also illustrative is an iron (II)-detecting test kit, which in addition to test strips includes a sample-measuring tube, a supply of a reducing agent for converting iron (III) to iron (II), and a measuring spoon for adding the appropriate quantity of reducing agent to the sample volume. "Total copper" by which is meant copper (II) and copper (I), or "total iron" by which is meant iron (III) and iron (II), are measured by these particular analyses.

An immersible reagent strip including an aperture, and a carrier having exposed opposite faces, is described in U.S. Pat. No. 5,491,094, which issued on Feb. 13, 1996 on application Ser. No. 08/253,959, filed on Jun. 3, 1994. An immersible test strip including a wick member enclosed in a fluid impervious sheath, and an aperture exposing a portion of the wick member, is illustrated by U.S. Pat. No. 4,092,115.

Also known as exemplified by U.S. Pat. No. 3,901,657, is an immersible test strip having a plurality of superposed carriers. Likewise known as illustrated by U.S. Pat. Nos. 3,006,735, 4,275,031, and 4,904,605, is a test strip having a plurality of spaced apart carriers affixed to or coated onto a support for multiple analyses upon immersion in a water sample.

There continues to be a need for an improved immersible colorimetric test strip, and in particular an improved immersible test strip for quantitative analysis of copper (I) or iron (II), and especially of total copper or total iron. Beneficially, there would be enhanced sensitivity and accuracy, yet simplicity of handling. It would be advantageous for the test strip to be economical to manufacture.

SUMMARY OF THE INVENTION

In accordance with the present invention, a unique colorimetric test strip for immersion in an aqueous sample, test kit, and method of using the test kit are provided. The test strip includes a support, and a colorimetric indicator-bearing, flow through carrier attached to a first region of the support. Beneficially, the support is provided with an aperture exposing a face of the carrier, which is water-permeable and has an exposed opposite face, permitting fluid flow through the carrier.

In accordance with the invention, separately attached to a second region of the support in a lateral relationship to the first region but not in fluid communication on the support with the indicator-bearing carrier, is a water absorbent carrier bearing an agent for chemically modifying analyte to enable detection by the colorimetric indicator. The analyte-modifying agent is present in an amount sufficient to chemically convert analyte in the aqueous sample to a detectible ionic form. In accordance with a preferred aspect of the invention, the analyte-modifying agent may be a reducing agent, in particular a water-soluble, reducing agent, and when the colorimetric indicator is capable of detecting copper (I) ions or iron (II) ions, the test strip is useful for quantitative analysis of total copper or total iron.

Also in accordance with the present invention, there is provided a test kit that includes the previously-described test strip, and a sample-measuring container. In accordance with the invention, an appropriate volume of an aqueous sample is added to the sample-measuring container, and the indicator-bearing carrier and the carrier bearing the analyte-modifying agent are immersed in the sample. Thereafter, the test strip is moved in the sample so as to assist chemical modification of the analyte by the analyte-modifying agent and to cause the sample to flow through the indicator-bearing carrier. Sufficient time is provided to allow analyte to be converted into a detectible ionic form and for the color-forming reaction. After this period of time has elapsed, the indicator-bearing carrier is removed from the sample and evaluated for detectable color change.

In the drawing and in detailed description of the invention that follows, there are essentially shown and described only preferred embodiments of this invention, simply by way of illustration of the best mode contemplated of carrying out this invention. As will be realized, this invention is capable of other and different embodiments, and its several details are capable of modification in various respects, all without departing from the invention. Accordingly, the drawing and the detailed description are to be regarded as illustrative in nature, and not as restrictive.

BRIEF DESCRIPTION OF THE DRAWING

Reference is now made to the accompanying drawing, which forms a part of the specification of the present invention.

FIG. 1 is a perspective view of a preferred test strip in accordance with the present invention;

FIG. 2 is a longitudinal cross-sectional view of the test strip of FIG. 1; and

FIG. 3 is a perspective view of a test kit in accordance with the present invention, which includes a second embodiment of a preferred test strip.

DETAILED DESCRIPTION OF THE INVENTION

As will become understood, the present invention combines improvements in sensitivity and accuracy, with simplicity of handling. Moreover, visually uniform color change is typically observable. In accordance with the present invention, analyte is chemically modified by a modifying substance carried on a test strip, and the modified analyte is thereafter detected by a colorimetric indicator carried on the test strip. Particularly beneficial applications are for the analysis of total copper or total iron in water samples.

Referring to FIGS. 1 and 2 of the drawing, a preferred colorimetric test strip or reagent strip 10 in accordance with the present invention, is shown. Strip 10 conveniently includes a support or handle member 12, which is typically a rigid plastic strip or stick for providing stiffness. Typically, the support is water-impermeable and ranges in thickness from about 0.008 to 0.020 inches; however, as will be understood, the thickness may, if appropriate, vary from this range. It will be understood that the term "strip" as used herein, is not limited to an elongated strip-like shape, for the reason that such a shape is immaterial to the invention.

Various thermoplastic materials may be used as the support, with preferred materials for economy being available at low cost, for instance, recycled resins. Suitably, the support may be made of, for example, PVC or polyester. It is generally preferable that the support is white, but as can be readily appreciated, the support may be colored by for instance, treatment with a dye.

A test strip in accordance with the present invention, beneficially permits liquid flow through an indicator-bearing carrier. As will become clear, it is highly advantageous for the carrier not to be limited by the volume of liquid it can absorb. To provide for liquid flow through a carrier, an aperture 14 is provided at or near an end 22 of the water-impermeable support. The aperture may have a variety of shapes such as oval, oblong, round, square, rectangular, star, triangular and diamond. Advantageously, unlike U.S. Pat. No. 3,006,735, the aperture is limited in size to effectively direct flow through a limited area. Typically, the aperture, when round, will be about 1/8" to 1/2" in diameter. When oblong, suitable dimensions are 1/4"×3/16".

Attached to the support and located so as to be exposed by the aperture, is a carrier 16, which is water-permeable. The carrier will typically have a thickness of about 0.002 to 0.02 inch, with a thickness of about 0.01 inch generally being particularly suitable.

Conveniently, a face 18 of the permeable carrier is attached to the support. Referring now particularly to FIG. 2, to enable liquid flow through the aperture and carrier, a face 20 of the carrier advantageously directly opposite to the exposed portion (as defined by aperture 14) of face 18, is beneficially exposed or uncovered. For purposes of this description, by "face" is meant a principal or wide surface of a member, as opposed to a narrow surface or edge such as the edge of U.S. Pat. No. 3,510,263.

As may be readily appreciated, a suitable water-permeable carrier will maintain its structural integrity during use. Materials useful as the carrier are well known, and include rayon, nitrocellulose and polyester filtration materials. A rayon filtration material commercially available as Scheicher and Schuell 8-S filter paper, is particularly useful. Other useful materials include woven or matted glass fiber, nonwoven and woven fabrics, and other filter papers. It will be understood that other water-permeable matrices that maintain structural integrity in use, may be useful.

With continued reference to FIG. 2, beneficially separately attached to a face 24 of the support and conveniently spaced apart from carrier 16 is an absorbent carrier 26. Carrier 26 is not in a superposed or layered relationship with carrier 16, but rather is in a side-by-side relationship. If desired, carriers 16,26 may be substantially contiguous to each other, that is, with minimum spacing between them, or carrier 26 may be attached to an opposite face 28 of the support.

Carrier 26 is conveniently a typical absorptive carrier of any suitable material known to the art, for example, filtration paper, and as such, will rapidly absorb the liquid being analyzed. As indicated, no corresponding aperture is needed in the support for absorbent carrier 26; thus, as in typical in the art, absorbent carrier 26 is suitably backed by a water-impermeable support. As will become understood, absorbent carrier 26 serves a different purpose than carrier 16, and thus will typically be of greater mass, and in particular, as indicated in FIG. 2, of relatively greater thickness. A convenient thickness for carrier 26 will range from about 0.02 to 0.05 inch. If desired or appropriate, the support may have attached to opposite face 28, an additional absorbent carrier member 26'.

Referring again to FIG. 1, deposited on or covalently or otherwise bound to carrier 16 is a colorimetric indicator (represented as dots), which may be one or more indicators. The colorimetric indicator may be organic or inorganic, but in any event will be suitable for the ion to be analyzed. Unless bound to carrier 16, it is beneficial for the indicator to be insoluble in or not readily soluble in water. Indicators useful for analysis of copper ions include 5-(4-dimethylaminobenzylidene)rhodanine, and useful for analysis of iron ions include 2,4,6-tri(2-pyridinyl)-1,3,5-triazine (TPTZ). Other suitable indicators may be selected. The indicator is suitably present on carrier 16 in an amount sufficient to ensure conversion of detectible analyte ions in the sample volume, to a colored complex.

Referring again to FIG. 2, in accordance with the present invention, carrier 26 is impregnated with or otherwise carries an analyte-modifying agent for chemical modification of the analyte prior to the color-forming reaction. For providing total copper or total iron analysis, a reducing agent is advantageously used. Useful reducing agents effective for converting copper (II) to copper (I), and iron (III) to iron (II), include ascorbic acid and hydroxylamine salts such as hydroxylamine hydrochloride. Ascorbic acid is particularly beneficial because it is water soluble and assists in appropriate pH adjustment. In certain analyses, a suitable oxidizing agent may be chosen as the analyte-modifying agent. However, in any event, an analyte-modifying agent will be chosen that does not interfere with the colorimetric indicator. More than one analyte-modifying agent may be used if desired or appropriate.

The amount of analyte-modifying agent needed, will vary depending upon factors including the type of sample, the modifying agent selected and the sample volume. For total copper or total iron analysis, the reducing agent is advantageously present in an amount sufficient to convert higher valence copper or iron cations in the sample volume to detectible, lower valence cations. To this end, a suitable loading of ascorbic acid will range from about 0.1 to 0.3 grams per sq. inch of carrier 26, with a loading of about 0.15 grams per sq. inch being satisfactory. A lower loading could, of course, be used; however, it is generally beneficial to saturate the carrier with the ascorbic acid.

Depending upon the concentration of analyte requiring chemical conversion, it may be convenient for the test strip to include additional absorbent carrier mass in the form of second absorbent carrier 26', bearing analyte-modifying agent, which is represented as dots on carrier 26' in FIG. 1. Alternatively, of course, carrier 26 could be of relatively greater mass. If too high a concentration of analyte requiring chemical conversion is present, the sample may be diluted, in which case the dilution factor must be considered.

As indicated, it may be beneficial to optimize the pH of the sample for improved reactivity and more accurate and/or sensitive results. A pH in the range of about 2 to 6, preferably about 3, is typically beneficial for copper or iron analysis using the previously described indicators. As mentioned, when ascorbic acid is the reducing agent, pH adjustment is benefitted. If further pH adjustment is appropriate when using ascorbic acid, an additional compatible, pH-adjusting additive may be used in an effective amount.

Referring now to FIG. 3, a preferred test strip 110 in accordance with the present invention is shown. This test strip is identical to test strip 10, except that the strip includes an additional aperture 144 and an additional indicator-bearing carrier 146. For sake of brevity, like parts have been indicated with like numbers.

Advantageously, carriers 116 and 146 are impregnated with or otherwise carry different indicators. Thus, carrier 116 may be impregnated with a copper indicator, and carrier 146 may be impregnated with an iron indicator. Beneficially, this test strip may be therefore used to detect copper and iron cations simultaneously, with the reducing agent on the two absorbent carriers (only carrier 126' shown) serving to reduce copper (II) and iron (III). As may be understood, additional absorbent carrier mass may be provided as appropriate, in the form of additional carriers disposed for instance, above aperture 144.

Deposition or carrier impregnation may be accomplished in any of several ways. A suitable way is to pass the carrier material through an impregnation bath containing the particular chemicals so that the carrier becomes saturated with the impregnation solution. The carrier may be then dried at room temperature or at an elevated temperature. For purposes of this invention, the terms "deposition" and "impregnation" are used interchangeably. Thus, any technique may be used that deposits the test chemicals on and/or impregnates the carrier.

Advantageously, the concentration of the colorimetric indicator in an impregnation solution and the residence time of the carrier material in the solution are selected to ensure deposition of an appropriate amount of the indicator. Generally speaking, the residence time will vary from about two to thirty seconds, depending upon the colorimetric indicator and carrier. If desired or appropriate, the carrier material may be dipped more than once to increase the concentration of the indicator. In any case, the amount of indicator deposited will be sufficient for colorimetric determination of the ion of interest.

As appropriate, the indicator-containing solution may include one or more organic or inorganic buffers for providing a suitable pH to the sample. As will be understood, a useful buffer will not form an interfering complex with the cation being detected. Depending upon the ion of interest, exemplary useful inorganic buffers include phosphate buffers such as monosodium phosphate, disodium phosphate and trisodium phosphate.

Advantageously, the solution containing the indicator, may include an additive for improved color development. In this respect, an additive such as propyl gallate, has been found useful in the analysis of copper and iron cations using the previously mentioned indicators.

This solution may also beneficially include a wetting agent for improved wetting of the carrier. Illustrative is a polyethoxylated fatty alcohol, nonionic surfactant commercially available from Rhone-Poulenc under the name Rhodasurf ON870. Other suitable wetting agents, with suitability depending upon the carrier selected, include an anionic surfactant such as dioctyl sodium sulfosuccinate.

In addition, the solution containing the indicator, may include a stabilizing agent for preventing undesired degradation of the indicator. Illustrative is an interpolymer of a lower alkylvinyl ether, and a lower alkyl-substituted or unsubstituted, 1,2-ethylenedicarboxylic acid lower alkyl monoester. Particularly useful is an interpolymer of methylvinyl ether and maleic acid isopropyl monoester, which is commercially available as Gantrez® ES-335-I.

In addition, when using ascorbic acid as the reducing agent, it may be beneficial to impregnate the reducing agent-bearing carrier with a polymeric film former such as polyvinyl pyrrolidone. Advantageously, when the reducing agent is water soluble, the film former is water soluble so as not to interfere with dissolution of the reducing agent in the sample. Particularly useful is polyvinyl pyrrolidone having an average molecular weight of 60,000 and commercially available from ISP Technologies, Incorporated as PVP K-60 Solution (PVP-60). In such case, the reducing agent solution will include a useful amount of a suitable polymeric film polymer.

If necessary or desired, one or more coagents or agents otherwise assisting in the analysis, may also be deposited on an indicator-bearing carrier or an analyte modifying agent-bearing carrier. As will be understood, an appropriate amount thereof will vary depending upon the colorimetric indicator and other considerations.

Attachment of a carrier to the support may be accomplished in a variety of ways. A suitable way is by use of a double-faced adhesive material. The adhesive material is layered down onto the support with tape liner on top. The aperture may then be punched out, the tape liner removed, and the carrier affixed by the adhesive surrounding the aperture. Other suitable methods for attaching a carrier to the support include heat sealing and ultrasonic sealing. It will be understood that the method of attachment is not limited to the methods just described.

Advantageously, with continued reference to FIG. 3, a test kit in accordance with the present invention, includes a container 150 of a suitable diameter and volumetric capacity, for measuring a standard volume of sample. Conveniently, as shown, the sample-measuring container may be a cylindrically-shaped, transparent vial, and includes a volume-indicating mark 152. The location of line 152 is selected to produce a level of sample that results in the indicator-bearing and reducing agent-bearing carriers being immersed in the sample. To this end, a convenient inner diameter of vial 150 is ½" and a suitable sample volume is 5.5 ml. In addition, the sample volume is beneficially limited so that the amounts of the analyte-modifying agent and other chemicals on the test strip, are sufficient for the intended purposes.

The time of contact of the sample with the test strip, is selected to provide sufficient time for dissolution of a water-soluble, analyte-modifying agent, chemical modification of the analyte by the analyte-modifying agent, and subsequent color development of the indicator. Typically, the time will vary from about 10 to 60 seconds, with about 20 to 40 seconds being useful when using ascorbic acid as the reducing agent in a copper or iron analysis.

Advantageously, the carriers are immersed in the sample to be analyzed, and the test strip is moved within the sample to assist dissolution of a water-soluble, analyte-modifying agent and to cause the sample to flow through the indicator-bearing carrier. The test strip may be moved within the sample in a variety of useful ways, for instance, back and forth or using a rotational or swirling motion, with it being particularly beneficial to cause flow through the aperture and thereby flowing contact of the sample with indicator on the carrier. As may be understood, rigidity of the support when wet assists effective movement of the test strip within the sample. Uniformity of color development in the area of the indicator-bearing carrier defined by the aperture, is typically observed.

After the selected contact time, the indicator-bearing carrier is evaluated for detectable color change. Beneficially, with respect to the embodiment of FIG. 1, color is evaluated from the aperture side of strip 10.

The following examples illustrate the present invention. In these examples and throughout this description, all parts and percentages are weight percent unless otherwise specified.

EXAMPLE 1

The following ingredients are combined in the order listed, as now described:

| | |
|---|---|
| 5-(4-dimethylaminobenzylidene) rhodanine | 0.2 g |
| Acetone | 200.0 g |
| Methanol | 40.0 g |
| L-Ascorbic Acid | 2.0 g |
| Propyl Gallate | 2.4 g |
| 10% Rhodasurf ON870 in ethanol | 2.72 g |

The indicator is dissolved in acetone and thereafter combined with methanol. The ascorbic acid is dissolved in the resulting mixture, following which propyl gallate is dissolved. Then, ON870 is added and the mixture is stirred until uniform. Immediately thereafter, 0.01" thick filter paper commercially available as Scheicher and Schuell 8-S filter paper, is immersed in the resulting mixture for five seconds, and then dried.

The following ingredients are combined to prepare the reducing agent solution.

| | |
|---|---|
| L-Ascorbic Acid | 1000.0 g |
| Distilled Water | 3000.0 g |
| PVP-60 (60%) | 70.0 g |

To prepare the reducing agent solution, the ascorbic acid is dissolved in the water, and then the PVP-60 is added. A clear solution results. Thereafter, 0.035" thick filter paper commercially as #222 paper from Ahlstrom, is impregnated with the reducing agent solution by immersion for about five seconds, and then dried.

A portion of the impregnated, dried indicator-bearing filter paper is disposed over an ¼"×³⁄₁₆" oblong aperture in a rigid, white PVC support and attached to the support by ultrasonic welding. A ⁵⁄₁₆"×½" portion of the reducing agent-impregnated, filter paper is attached by double-faced adhesive tape to one face of the support, and thereafter a second portion is attached to the other support face. The support is approximately 0.012" thick, ⁵⁄₁₆" wide and 3" long.

Fresh copper standards are prepared gravimetrically from copper (II) sulfate using tap water, with levels of 0.5, 1.0, 2.0, 5.0 and 10 ppm. Tap water is used as the control and is assigned a value of 0 ppm copper.

An analysis using test strips prepared in the manner described, is carried out as follows. In sequence, the various liquids to be analyzed are poured into the sample-measuring, transparent, cylindrical vial until the liquid level reaches the 5.5 ml mark. A test strip is immersed in each sample for 30 seconds using gentle back and forth motion, thereafter removed, and within ½ minute, the carrier color in the area defined by the aperture, is visually compared to a color chart and matched to the closest match. Color uniformity is observed in the area defined by the aperture. The results (total copper) are shown in Table 1, column headed "Aperture Motion". Sample pH is measured, and the average sample pH (after analysis) is found to be about 3.

COMPARATIVE EXAMPLE 1

Test strips are prepared as in Example 1, with changes as follows: The PVC support lacks an aperture, and the indicator-impregnated, filter paper is attached to the support using double-faced, adhesive tape. Using the copper standards and control of Example 1, the analysis method of Example 1 is followed except that the strips are immersed for 30 seconds without any motion. The colors appear to be essentially identical and to be between 0 and

TABLE 1

| Copper (ppm) | Aperture Motion | No Aperture Motion | No Aperture No Motion |
|---|---|---|---|
| 0 | 0 | 0 | 0* |
| 0.5 | 0.5 | 0 | 0* |
| 1.0 | 1.0 | 0 | 0* |
| 2.0 | 2.0 | 0.5 | 0* |
| 5.0 | 5.0 | 2.0 | 0* |
| 10.0 | 10.0 | 2.0 | 0* |

*See text

TABLE 2

| Iron (ppm) | Aperture Motion | No Aperture Motion | No Aperture No Motion |
|---|---|---|---|
| 0 | 0 | 0 | 0 |
| 0.5 | 0.3 | 0 | 0 |
| 1.0 | 0.5 | 0.3* | 0 |
| 2.0 | 1.0 | 0.3* | 0 |
| 5.0 | 5.0 | 1.0* | 0.3* |
| 10.0 | 5.0 | 1.0* | 0.5* |

*Not uniform in color 0.5 ppm, but closer to 0. The results are given as 0 in the column headed "No Aperture No Motion", in Table 1.

Again using the copper standards and control of Example 1, the analysis method of Example 1 is followed except that the strips are immersed for 30 seconds using gentle back and forth motion as in Example 1. The results are found in the column headed "No Aperture Motion", in Table 1.

As demonstrated in Table 1, sensitivity and as a result accuracy, are markedly enhanced by a flow through, indicator-bearing carrier. Even using identical motion, less sensitivity and accuracy are obtained when the indicator-bearing carrier is backed by a water-impermeable member that prevents flow through the carrier faces. It is highly advantageous for the carrier not to be limited by the volume of liquid it can absorb, particularly as in the present invention when chemical modification of an analyte precedes the color-forming reaction and the indicator-bearing carrier is immersed in the sample prior to the chemical modification. As may be understood, the reducing agent is solubilized from its carrier into the sample.

EXAMPLE 2

The following ingredients are combined in the order listed, as now described:

| | |
|---|---:|
| TPTZ | 0.9 g |
| Methanol | 285.0 g |
| L-Ascorbic Acid | 3.0 g |
| Hydroxylamine HCl | 3.0 g |
| Propyl Gallate | 1.5 g |
| Sodium Thiosulphate | 3.0 g |
| Water, distilled | 6.0 g |
| 10% Rhodasurf ON870 in ethanol | 2.25 g |

TPTZ is dissolved in the methanol, and thereafter in sequence, the next three listed ingredients are dissolved in the methanol. Sodium thiosulphate is dissolved in the water, and the resulting aqueous solution is added to the methanol. Then, ON870 is added and the mixture is stirred until a clear, uniform solution is obtained. Immediately thereafter, 0.01" thick filter paper commercially available as Scheicher and Schuell 8-S filter paper, is immersed in the clear solution for about five seconds, and then dried.

The reducing agent solution is made as in Example 1. Thereafter, #222 filter paper from Ahlstrom, is impregnated with the reducing agent solution and dried as in Example 1.

A portion of the impregnated, dried TPTZ-bearing filter paper is disposed over an ¼"×3/16" oblong aperture in a rigid, white PVC support and attached to the support by ultrasonic welding. A 5/16"×½" portion of the reducing agent-impregnated, filter paper is attached by double-faced adhesive tape to one face of the support, and thereafter a second portion is attached to the other support face. The support is approximately 0.012" thick, 5/16" wide and 3" long.

Fresh iron standards from iron (III) nitrate, are prepared using well water, with levels of 0.5, 1.0, 2.0, 5.0 and 10.0 ppm. The iron levels are confirmed using a Hach reference method (Hach Cat. No. 1464-00, model IR-18, range 0 to 5 mg/L); the 10 ppm standard is diluted prior to evaluation by the reference method and the dilution factor is taken into consideration. Well water is used as the diluent, and is verified to have a value of 0 ppm iron.

An analysis using test strips prepared in the manner described, is carried out as follows. In sequence, the various liquids to be analyzed are poured into a sample-measuring, transparent, cylindrical vial having an inner diameter of ½", until the liquid level reaches the 5.5 ml mark on the vial. A test strip is immersed in each sample for 30 seconds using gentle back and forth motion, thereafter removed, and after 2 minutes the carrier color in the area defined by the aperture, is visually compared to a color chart developed for iron (II), and matched to the closest match. Color uniformity is observed in the area defined by the aperture. The results (total iron) are shown in Table 2, column headed "Aperture Motion". Sample pH is measured, and the average sample pH (after analysis) is found to be about 3.

COMPARATIVE EXAMPLE 2

Test strips are prepared as in Example 2, with changes as follows: The PVC support lacks an aperture, and the TPTZ-impregnated, filter paper is attached to the support using double-faced, adhesive tape. Using the iron standards and control (well water) of Example 2, the analysis method of Example 2 is followed except that the strips are immersed for 30 seconds without any motion. The results are given in the column headed "No Aperture No Motion", in Table 2. As indicated in Table 2, color uniformity on the TPTZ-impregnated, filter paper is lacking, and matching is therefore difficult.

Again using the iron standards and control of Example 2, the analysis method of Example 2 is followed except that the strips are immersed for 30 seconds using gentle back and forth motion as in Example 2. The results are given in the column headed "No Aperture Motion" in Table 2. As indicated in Table 2, color uniformity on the TPTZ-impregnated, filter paper is again lacking, and matching is therefore again difficult.

Because the iron (III) references are unstable, the analyses of Example 2 and Comparative Example 2 are carried out substantially simultaneously.

Table 2 demonstrates that sensitivity and accuracy are markedly enhanced by a flow through, indicator-bearing carrier. Even using identical motion, less sensitivity and accuracy are obtained when the indicator-bearing carrier is backed by a water-impermeable member that prevents flow through the carrier faces.

The present invention may be carried out with various modifications without departing from the spirit or essential attributes thereof, and accordingly, reference should be made to the appended claims, rather than to the foregoing specification as indicating the scope of the invention.

What is claimed is:

1. A colorimetric test strip comprising a support, a colorimetric indicator-bearing, water-permeable, first carrier attached to said support in a first region, wherein said support is provided with an aperture exposing a first face of said indicator-bearing carrier, which has an exposed second face permitting fluid flow therethrough, and attached to said support in a second region in a lateral relationship to said first region but not in fluid communication on said support with said indicator-bearing carrier, a water absorbent, second carrier bearing an effective amount of an analyte-modifying agent for converting a selected analyte in an aqueous sample from an ionic valence state undetectible by said indicator to a detectible valence state.

2. The colorimetric test strip of claim 1, wherein said analyte-modifying agent is a reducing agent.

3. The colorimetric test strip of claim 1, wherein said analyte-modifying agent is water soluble.

4. The colorimetric test strip of claim 2, wherein said reducing agent comprises ascorbic acid.

5. The colorimetric test strip of claim 1, wherein said colorimetric indicator is capable of detecting copper (I) ions, and said analyte-modifying agent is a reducing agent comprising ascorbic acid.

6. The colorimetric test strip of claim 1, wherein said colorimetric indicator is capable of detecting iron (II) ions, and said analyte-modifying agent is a reducing agent comprising ascorbic acid.

7. The colorimetric test strip of claim 1, further comprising a colorimetric indicator-bearing, water-permeable, third carrier attached to said support, wherein said support is provided with a second aperture exposing a first face of said indicator-bearing, third carrier, which has an exposed second face permitting fluid flow therethrough.

8. A test kit comprising the test strip of claim 1 and a sample-measuring container of a suitable volumetric capacity.

9. An analysis method using the test strip of claim 1, wherein said analyte-modifying agent is water soluble; said analysis method comprising adding an appropriate volume of an aqueous sample to a sample-measuring container, immersing said aperture of said support and said carrier bearing said analyte-modifying agent in said sample volume, and moving said test strip in said sample to assist dissolution of said analyte-modifying agent in said sample and to cause said sample to flow through said aperture, for a period of time sufficient to allow said analyte to be converted to said detectible valence state by said analyte-modifying agent and to allow thereafter for said analyte in said detectible valence state to be detected by said indicator; removing said indicator-bearing carrier from said sample; and evaluating said indicator-bearing carrier for detectable color change.

10. The method of claim 9, wherein said period of time is in the range of about 20 to 40 seconds.

11. The method of claim 10, wherein said sample is selected from pool water and spa water.

12. The colorimetric test strip of claim 1, wherein said aperture is completely bounded by said support.

13. The colorimetric test strip of claim 1, wherein said aperture is limited in size to effectively direct flow through a limited area.

14. The colorimetric test strip of claim 1, wherein said second carrier is of greater mass than said indicator-bearing carrier.

15. The colorimetric test strip of claim 1, wherein said first carrier and said second carrier are in a spaced apart relationship.

16. The colorimetric test strip of claim 15, wherein said support comprises a first face and a second face, and wherein first carrier and said second carrier are attached to said first face of said support.

17. The colorimetric test strip of claim 7, wherein said indicator on said third carrier is different than said indicator on said first carrier.

18. The colorimetric test strip of claim 17, wherein said analyte-modifying agent is a reducing agent capable of converting a second selected analyte in said aqueous sample from an ionic valence state undetectible by said indicator on said third carrier, to a valence state detectible by indicator on said third carrier.

19. A colorimetric test strip comprising a support, a colorimetric indicator-bearing, water-permeable, first carrier attached to said support in a first region, wherein said support is provided with an aperture exposing a first face of said indicator-bearing carrier, which has an exposed second face permitting fluid flow therethrough, and wherein said aperture is completely bounded by said support, and attached to said support in a second region in a lateral relationship to said first region but not in fluid communication on said support with said indicator-bearing carrier, a water absorbent, second carrier bearing an effective amount of a water soluble, reducing agent for converting a selected analyte in an aqueous sample from an ionic valence state undetectible by said indicator to a detectible valence state, wherein said first carrier and said second carrier are in a spaced apart relationship.

* * * * *